US010548995B2

(12) United States Patent
Skjold et al.

(10) Patent No.: US 10,548,995 B2
(45) Date of Patent: Feb. 4, 2020

(54) RADIOLABELLING METHOD

(71) Applicant: GE Healthcare Limited, Buckinghamshire (GB)

(72) Inventors: Willy Skjold, Oslo (NO); Bard Indrevoll, Oslo (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 14/907,955

(22) PCT Filed: Aug. 20, 2014

(86) PCT No.: PCT/EP2014/067775
§ 371 (c)(1),
(2) Date: Jan. 27, 2016

(87) PCT Pub. No.: WO2015/024983
PCT Pub. Date: Feb. 26, 2015

(65) Prior Publication Data
US 2016/0166717 A1  Jun. 16, 2016

(30) Foreign Application Priority Data
Aug. 21, 2013  (GB) .................................. 1314936.4

(51) Int. Cl.
| *A61K 51/08* | (2006.01) |
| *C07K 1/16* | (2006.01) |
| *C07K 1/20* | (2006.01) |
| *B01J 19/24* | (2006.01) |
| *C07K 1/13* | (2006.01) |
| *C07K 14/00* | (2006.01) |

(52) U.S. Cl.
CPC .............. *A61K 51/08* (2013.01); *B01J 19/24* (2013.01); *C07K 1/13* (2013.01); *C07K 1/20* (2013.01); *C07K 14/001* (2013.01); *B01J 2219/24* (2013.01); *C07K 2318/00* (2013.01)

(58) Field of Classification Search
CPC ....... A61K 51/088; C07K 14/001; C07K 1/13
See application file for complete search history.

(56) References Cited

U.S. PATENT DOCUMENTS

| 5,961,955 | A | 10/1999 | Shochat et al. |
| 7,597,875 | B2 | 10/2009 | Archer et al. |
| 7,902,332 | B2 | 3/2011 | De Jesus et al. |
| 8,044,175 | B2 | 10/2011 | Dransfield et al. |
| 8,197,793 | B2 | 6/2012 | Cuthbertson et al. |
| 8,431,111 | B2 | 4/2013 | Nairne et al. |
| 8,435,454 | B2 | 5/2013 | Elizarov et al. |
| 8,529,874 | B2 | 9/2013 | Johannesen et al. |
| 8,557,776 | B2 | 10/2013 | Lehmann et al. |
| 8,568,693 | B2 | 10/2013 | Danikas et al. |
| 9,000,124 | B2 | 4/2015 | Dransfield et al. |
| 9,259,496 | B2 | 2/2016 | Iveson et al. |
| 9,533,059 | B2 | 1/2017 | Iveson et al. |
| 9,956,303 | B2 | 5/2018 | Dalsgaard et al. |
| 2009/0274623 | A1 | 11/2009 | Smith et al. |
| 2010/0068150 | A1 | 3/2010 | Bogyo et al. |
| 2013/0149241 | A1 | 6/2013 | Iveson et al. |
| 2013/0209358 | A1 | 8/2013 | Barnett et al. |
| 2014/0004041 | A1 | 1/2014 | Iveson et al. |
| 2014/0335022 | A1 | 11/2014 | Dalsgaard et al. |
| 2016/0303262 | A1 | 10/2016 | Engell et al. |
| 2016/0303263 | A1 | 10/2016 | Engell et al. |

FOREIGN PATENT DOCUMENTS

| EP | 1952826 A1 | 8/2008 |
| EP | 2287197 A1 | 2/2011 |
| EP | 2605802 B1 | 6/2013 |
| EP | 3036208 A1 | 6/2016 |
| JP | 2009542689 A | 12/2009 |
| JP | 2010520229 A | 6/2010 |
| JP | 2010526859 A | 8/2010 |
| JP | 2011513211 A | 4/2011 |
| JP | 5309141 B2 | 10/2013 |
| JP | 5341757 B2 | 11/2013 |
| JP | 6014592 B2 | 10/2016 |
| WO | 02070018 A2 | 9/2002 |
| WO | 03006070 A2 | 1/2003 |
| WO | 03057155 A2 | 7/2003 |
| WO | 2004062568 A2 | 7/2004 |
| WO | 2004078778 A2 | 9/2004 |
| WO | 2004080492 A1 | 9/2004 |
| WO | 2006030291 A2 | 3/2006 |
| WO | 2008072976 A2 | 6/2008 |

(Continued)

OTHER PUBLICATIONS

Search Report regarding GB Application No. 1314936.4, dated Feb. 14, 2014, 3 pages.
English translation of Chinese First Search Report from Chinese Patent Appl. No. 201480046209.X, filed Aug. 20, 2014.
English translation of First Office Action for Chinese Patent Appl. No. 01480046209.X, filed Aug. 20, 2014, 11 pages, dated Dec. 5, 2016.
International Search Report and Written Opinion regarding International Application No. PCT/EP2014/078609, dated Apr. 7, 2015, 15 pages.
GB Search Report regarding GB Application No. 1322456.3, dated Aug. 18, 2014, 3 pages.
International Search Report and Written Opinion regarding International Application No. PCT/EP2014/078608, dated Mar. 5, 2015, 8 pages.

(Continued)

*Primary Examiner* — James H Alstrum-Acevedo
*Assistant Examiner* — Kaipeen E Yang
(74) *Attorney, Agent, or Firm* — Arent Fox, LLP

(57) ABSTRACT

The present invention relates to the field of radiopharmaceuticals for in vivo imaging, in particular to a method of labelling a biological targeting molecule with the radioisotope $^{18}$F. The invention provides a method of preparation of lyophilised compositions of aminooxy-functionalised biomolecules, as well as radiolabelling methods using the purified materials. Also provided are lyophilised compositions and cassettes comprising such purified compositions. The invention is particularly suitable for use with an automated synthesizer apparatus.

7 Claims, No Drawings
Specification includes a Sequence Listing.

(56) References Cited

FOREIGN PATENT DOCUMENTS

| WO | 2008139207 A2 | 11/2008 |
|---|---|---|
| WO | 2009016180 A2 | 2/2009 |
| WO | 2009016181 A2 | 2/2009 |
| WO | 2009027706 A2 | 3/2009 |
| WO | 2009106566 A2 | 9/2009 |
| WO | 2011008990 A1 | 1/2011 |
| WO | 2011048029 A1 | 4/2011 |
| WO | 2012022676 A1 | 2/2012 |
| WO | 2012022676 A2 | 2/2012 |
| WO | 2012072728 A2 | 6/2012 |
| WO | 2012072736 A2 | 6/2012 |
| WO | 2012076697 A1 | 6/2012 |
| WO | 2012087725 A1 | 6/2012 |
| WO | 2012087912 A1 | 6/2012 |
| WO | WO 2012/072736 A2 | 6/2012 |
| WO | 2012/072736 A3 | 10/2012 |
| WO | 2013092742 A1 | 6/2013 |
| WO | 2013174909 A1 | 11/2013 |
| WO | 2015/024983 A1 | 2/2015 |
| WO | 2015024983 A1 | 2/2015 |

OTHER PUBLICATIONS

English translation of First Office Action for Chinese Patent Application No. 20140046209.X, filed Aug. 20, 2014, 11 pages, dated Dec. 5, 2016.

International Search Report and Written Opinion regarding International Application No. PCT/EP2014/067775, dated Dec. 17, 2014, 7 pages.

Japanese Office Action regarding JP Application No. 2013-524419, dated May 17, 2016 (English Translation attached).

Poethko et al., "Two-Step Methodology for High-Yield Routine Radiohalogenation of Peptides: 18F-Labled RGD and Octreotide Analogs", Journal of Nuclear Medicine, vol. 45, No. 5, May 2004 pp. 892-902.

International Search Report and Written Opinion regarding International Application No. PCT/EP2012/076196, dated Mar. 28, 2013.

Kilbourn et al., "Fluorine-18 Labeling of Proteins", J Nucl Med, 1987, pp. 462-470.

International Search Report and Written Opinion regarding International Application No. PCT/EP2011/063890, dated Dec. 19, 2011, 14 pages.

Great Britain Search Report regarding GB Application No. 1013808.9, dated Dec. 15, 2010.

Flavell et al. "Site-Specific 18F-Labeling of the Protein Hormone Leptin Using a General Two-Step Ligation Procedure", Journal of the American Chemical Society, 2008, vol. 1330, pp. 9106-9112.

Great Britain Search Report regarding GB Application No. 1103696.9, dated Aug. 10, 2011.

International Search Report and Written Opinion regarding International Application No. PCT/EP2012/053614, dated May 16, 2012, 10 pages.

Office Action received for Japanese Patent Application No. 2014-547982, dated Jan. 17, 2017, 4 pages (1 page English Communication + 3 pages Official Copy).

International Preliminary Report on Patentability received for PCT Patent Application No. PCT/EP2012/076196, dated Jun. 24, 2014, 8 pages.

Garcia, et al., "C-Met Overexpression in Inflammatory Breast Carcinomas: Automated Quantification on Tissue Microarrays", British Journal of Cancer, vol. 96, 2007, pp. 329-335.

Great Britain Search Report regarding GB Application No. 1121914.4, dated Apr. 30, 2012.

Office Action Received for Chinese Patent Application No. 201480046209.X, dated Aug. 18, 2017, 28 Pages (18 Pages of English Translation + 10 Pages Official Copy).

RADIOLABELLING METHOD

This application is a filing under 35 U.S.C. 371 of international application number PCT/EP2014/067775, filed Aug. 20, 2014, which claims priority to GB application number 1314936.4, filed Aug. 21, 2013, the entire disclosures of each of which are hereby incorporated by reference.

SEQUENCE LISTING

The instant application contains a Sequence Listing which has been filed electronically in ASCII format and is hereby incorporated by reference in its entirety. Said ASCII copy, created on Apr. 4, 2019, is named 037380_00040_SL.txt and is 7,546 bytes in size.

FIELD OF THE INVENTION

The present invention relates to the field of radiopharmaceuticals for in vivo imaging, in particular to a method of labelling a biological targeting molecule with the radioisotope $^{18}$F. The invention provides a method of preparation of lyophilised compositions of aminooxy-functionalised biomolecules, as well as radiolabelling methods using the purified materials. Also provided are lyophilised compositions and cassettes comprising such purified compositions. The invention is particularly suitable for use with an automated synthesizer apparatus.

BACKGROUND TO THE INVENTION

WO 2004/080492 A1 discloses a method for radiofluorination of a biological targeting vector, comprising reaction of a compound of formula (I) with a compound of formula (II):

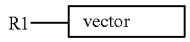

(I)

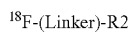

(II)

or,
a compound of formula (III) with a compound of formula (IV)

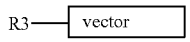

(III)

(IV)

wherein:
R1 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
R2 is a group selected from primary amine, secondary amine, hydroxylamine, hydrazine, hydrazide, aminooxy, phenylhydrazine, semicarbazide, and thiosemicarbazide;
R3 is a group selected from primary amine, secondary amine, hydroxylamine, hydrazine, hydrazide, aminooxy, phenylhydrazine, semicarbazide, or thiosemicarbazide;
R4 is an aldehyde moiety, a ketone moiety, a protected aldehyde such as an acetal, a protected ketone, such as a ketal, or a functionality, such as diol or N-terminal serine residue, which can be rapidly and efficiently oxidised to an aldehyde or ketone using an oxidising agent;
to give a conjugate of formula (V) or (VI) respectively:

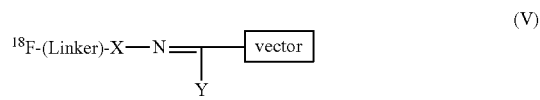

(V)

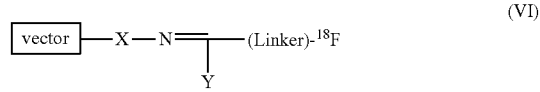

(VI)

wherein X is —CO—NH—, —NH—, —O—, —NHCONH—, or —NHCSNH—, and is preferably —CO—NH—, —NH— or —O—; Y is H, alkyl or aryl substituents; and
the Linker group in the compounds of formulae (II), (IV), (V) and (VI) is selected from:

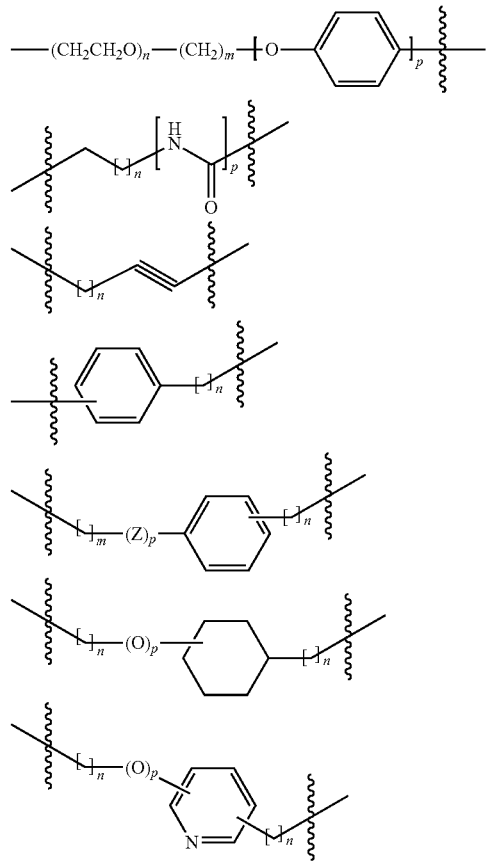

wherein:
n is an integer of 0 to 20;
m is an integer of 1 to 10;
p is an integer of 0 or 1;
Z is O or S.
Poethko et al [J. Nucl. Med., 45(5), 892-902 (2004)] disclose a method of radiolabelling peptides with the radioisotope $^{18}$F, wherein an aminooxy-functionalised peptide is condensed with [$^{18}$F]-fluorobenzaldehyde to give a labelled peptide having an oxime ether linkage as follows:

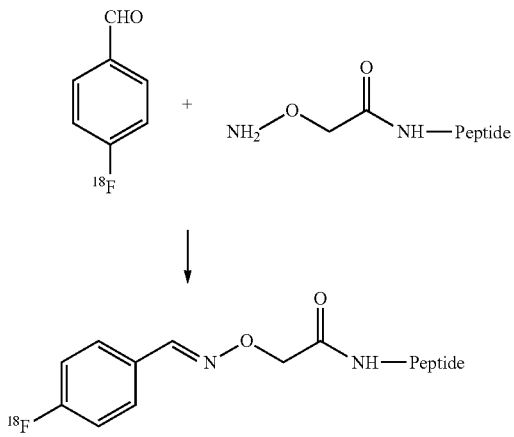

Schottelius et al [Bioconj. Chem., 19(6), 1256-1268 (2008)] further developed the method of Poethko et al. Schottelius et al use an aminooxy-functionalised peptide wherein the amine of the aminooxy group is protected with an N-Boc (Boc=tert-butyloxycarbonyl) protecting group. The desired aminooxy-functionalised peptide is generated in situ in the presence of [$^{18}$F]-fluorobenzaldehyde via deprotection of the N-Boc group at acidic pH (pH=2) at 75° C. Schottelius et al used a 5-fold molar excess of the Boc-protected precursor, because the deprotection was not quantitative under the reaction conditions.

Mezo et al [J. Pept. Sci., 17, 39-46 (2010)] describe some of the problems associated with the above oxime ligation chemistry of Boc-protected aminooxy-functionalised peptides. Thus, it is known that the Boc-aminooxy reagent can acylate formed Boc-protected aminooxy-peptide, leading to undesirable by-products. It is also known that the reactivity of the free aminooxy group of the functionalised peptide is high towards carbonyl compounds. Consequently, unwanted condensation can occur with any adventitious aldehydes or ketones present either in the reaction mixture or in any subsequent purification steps. Such aldehydes or ketones could be traces of acetone present in the solvents used, or formaldehyde (e.g. from plasticizers). Mezo et al are interested in solving this problem for both the conjugation of anti-cancer drugs and of [$^{18}$F]-fluorobenzaldehyde to peptides. Mezo et al solve the problem by carrying out the deprotection of the Boc-aminooxy peptide in the presence of a tenfold molar excess of free (aminooxy)acetic acid (Aoa) as a 'carbonyl capture agent'. The deprotected aminooxy-peptide and excess Aoa is then lyophilised and stored at 4° C. Immediately prior to the oxime ligation reaction, the lyophilised mixture is reconstituted, and excess Aoa is separated by HPLC or Sep-Pak plus C18 cartridge. Mezo et al provide an example in which non-radioactive (i.e. $^{19}$F) 4-fluorobenzaldehyde is conjugated to an aminooxy-functionalised somatostatin peptide using this technique. Mezo et al do not provide any data on $^{18}$F-radiolabelling.

WO 2012/072736 discloses the use of alternative protecting group chemistry for the aminooxy groups of functionalised biomolecules. The protected aminooxy group is of formula:

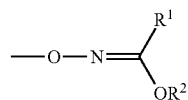

wherein R$^1$ and R$^2$ are independently chosen from C$_{1-3}$ alkyl, C$_{1-3}$ fluoroalkyl or C$_{4-6}$ aryl.

WO 2012/072736 teaches that it is preferred to deprotect the protected aminooxy group in situ, i.e. in the presence of the radioactive aldehyde to which it is to be conjugated without intermediate isolation. Example 3 of WO 2012/072736 does, however, disclose the deprotection of a peptide functionalised with such a protected aminooxy group, and subsequent direct lyophilisation to afford an isolated product. The lyophilised composition obtained directly was described as pure. WO 2012/072736 does not, however, recognise the problems of side reactions with acetate forming by-products as taught by the present invention.

There is therefore still a need for alternative or improved methods of preparing and radiolabelling peptides and other biological targeting molecules.

The Present Invention.

The present invention provides a method for preparing a lyophilised composition of a biological targeting molecule (BTM) having conjugated thereto an aminooxy functional group.

The invention provides purified aminooxy-functionalised BTMs as lyophilised compositions of such purified materials, and their subsequent use in radiolabelling. The invention provides a more efficient deprotection step due to increased solubilisation of the protected precursor. Since the deprotection occurs in the mobile phase used for chromatographic purification, the process is more efficient since there is no need to isolate the purified protected aminooxy derivative. This is particularly important since it saves a lyophilisation step, since the protected aminooxy derivative is typically isolated by lyophilisation which is a time-consuming process. Also, the lyophilised material is more readily dissolved when used for radiolabelling which is important for efficient labelling and purification of BTMs.

DETAILED DESCRIPTION OF THE INVENTION

In a first aspect, the present invention provides a method of preparation of an aminooxy-functionalised biological targeting molecule lyophilised composition which comprises:

(i) reverse phase chromatographic purification of a protected compound of Formula (IA):

using a mobile phase, to give purified Compound IA in said mobile phase; (ii) deprotection of the purified Compound IA from step (i), to give a solution of aminooxy compound of Formula (IIA):

(iii) lyophilisation of the solution from step (ii), to give a lyophilised composition of said aminooxy compound of Formula (IIA);

wherein:
[BTM] is a biological targeting molecule;
$X^1$ is a protected aminooxy group of formula:

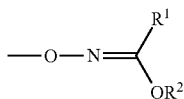

wherein $R^1$ and $R^2$ are independently chosen from $C_{1-3}$ alkyl, $C_{1-3}$ fluoroalkyl or $C_{4-6}$ aryl.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term "protected" has its conventional meaning in the field of chemistry and/or radiochemistry, and refers to the use of a protecting group to protect a functional group from unwanted reactions. The term "deprotection" has its conventional meaning in the field of chemistry and/or radiochemistry, i.e. the removal of a protecting group. By the term "protecting group" or $P^{GP}$ is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. The use of protecting groups is described in *Protective Groups in Organic Synthesis,* 4$^{th}$ Edition, Theorodora W. Greene and Peter G. M. Wuts, [Wiley Blackwell, (2006)].

The term "aminooxy group" has its conventional meaning, and refers to a substituent of formula —O—NH$_2$, preferably —CH$_2$—O—NH$_2$.

The term "reverse phase chromatographic purification" has its conventional meaning, and refers to chromatography where the stationary phase is lipophilic and the mobile phase is hydrophilic, typically involving aqueous media. Suitable chromatographic techniques include: HPLC, medium pressure liquid chromatography (MPLC) or solid phase extraction (SPE). A preferred reverse phase chromatographic technique is HPLC. Suitable RP-HPLC column materials are silica based and hence should be end-capped to avoid unwanted interactions with silanol groups on the surface of the particles. The column material should have high surface area coverage accepting moderate to high preparative loads of the substance to be purified and readily available packed in various column formats and also available in bulk for packing into larger preparative columns if larger quantities are needed. Preferred such HPLC columns include: Luna C-18 (2) (10 μm, 100 A) from Phenomenex; or other silica based C-18 materials such as Kromasil from Eka or ODS AQ from YMC. The HPLC column is most preferably a Luna C-18 (2) (10 μm, 100 A) column.

Deprotection step (ii) is suitably carried out as is known in the art [Dulery et al Tetrahedron, 63, 11952-11958 (2007); and Foillard et al [J. Org. Chem., 73, 983-991 (2008)].

Aldehydes and ketones should also suitably be excluded from steps (i)-(iii), since even in trace amounts or airborne in the laboratory atmosphere, they will undergo unwanted side reactions with the aminooxy compound of Formula IIA.

The term "lyophilised" has the conventional meaning, i.e. a freeze-dried composition, preferably one which is prepared in a sterile manner Preferred Features.

The mobile phase used in step (i) is preferably acidic. An acidic mobile phase has the advantage that, when the BTM comprises basic groups such as the amino groups of peptides or proteins, these are protonated in order to achieve adequate chromatographic separation.

Preferably the acid used in the mobile phase of step (i) comprises trifluoroacetic acid (TFA), and more preferably comprises aqueous TFA. A suitable TFA concentration in the mobile phase of step (i) is in the range 0.01-5%, preferably 0.05-1% more preferably 0.1-0.3% v/v. TFA has the advantage that it is volatile and easier to remove than ammonium acetate when preparing the lyophilised compositions of the second aspect.

Thus, using aqueous TFA as mobile phase for step (i), the present inventors have found that deprotection of compound IA does not occur to a meaningful extent during HPLC chromatography, since the contact time with the aqueous TFA mobile phase is short (20-40 min) and since the compound IA is bound to the stationary phase, and thus not accessible to deprotection. During storage in solution in the aqueous TFA mobile phase, however, with a contact time of few minutes deprotection does occur.

When the mobile phase is acidic, deprotection is preferably achieved by either standing the separated, purified Compound IA in the acidic mobile phase for a period of time at a temperature of 5 to 60° C. to permit reaction, and/or adding more acid to said solution. Thus, e.g. storage in 0.1% aqueous TFA at ambient temperature under Argon overnight showed about 0.8% remaining protected (Compound IA). Complete deprotection and/or shorter reaction times requires the addition of more TFA, e.g. 0.13-0.15% TFA.

Hence, step (i) of the first aspect is preferably carried out without isolation of the purified Compound IA, so that it is used in step (ii) as the solution in the mobile phase from step (i). This has the advantage of improved efficiency, since the present inventors have found that, if isolated (e.g. by lyophilisation), purified Compound IA tends to exhibit low solubility in the deprotection medium, necessitating its' use as a suspension even when diluted. That in turn leads to larger solvent volumes for lyophilisation in step (iii), which significantly extends the lyophilisation time and reduces the maximum batch size which can be processed each time. The capacity of the freeze-drier in terms of maximum volume to be processed usually dictates the batch size.

In the first aspect, $R^1$ and $R^2$ are preferably both independently $C_{1-2}$ alkyl. More preferably, $R^1$ and $R^2$ are chosen from methyl and ethyl, most preferably $R^1$ is methyl and $R^2$ is ethyl, i.e. an ethoxyethylidine ("Eei") protecting group.

The BTM may be of synthetic or natural origin, but is preferably synthetic. The term "synthetic" has its conventional meaning, i e man-made as opposed to being isolated from natural sources e.g. from the mammalian body. Such compounds have the advantage that their manufacture and impurity profile can be fully controlled. Monoclonal antibodies and fragments thereof of natural origin are therefore outside the scope of the term 'synthetic' as used herein. The molecular weight of the BTM is preferably up to 30,000 Daltons. More preferably, the molecular weight is in the range 200 to 20,000 Daltons, most preferably 300 to 18,000 Daltons, with 400 to 16,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

BTM preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligoDNA or oligo-RNA fragments. More preferably, BTM comprises either an AFFIBODY™, an antibody mimetic or a single amino acid, a 3-100 mer peptide, an enzyme substrate, an enzyme antagonist an enzyme agonist, an enzyme inhibitor or a receptor-binding compound.

By the term "peptide" is meant a compound comprising two or more amino acids, as defined below, linked by a peptide bond (i.e. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also *Synthesis of Peptides and Peptidomimetics*, M. Goodman et al, Houben-Weyl E22c, Thieme.

By the term "amino acid" is meant an L- or D-amino acid, amino acid analogue (e.g. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsi-peptides, retro-inverso peptides, thioamides, cycloalkanes or 1,5-disubstituted tetrazoles [see M. Goodman, Biopolymers, 24, 137, (1985)]. Radiolabelled amino acids such as tyrosine, histidine or proline are known to be useful in vivo imaging agents.

AFFIBODY™, an antibody mimetic molecules are based on the 58 amino acid residue domain derived from one of the IgG-binding domains of staphylococcal protein A. Affibodies may be used in monomer or dimer form, and have been reviewed by Nygren [FEBS J., 275, 2668-2676 (2008)] and Nilsson et al [Curr. Opin. Drug. Disc. Dev., 10, 167-175 (2007)]. The relatively small size of these Affibodies should allow better target tissue penetration and blood clearance compared to antibodies which are 10 to 20 times larger (~150 kDa). Affibodies also have the advantage that they are stable under a range of pH conditions (pH 5 0.5 to 11). A preferred Affibody of the invention targets HER2. A preferred HER2 targeting Affibody comprises Affibody 1, as described below.

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, i.e. an amide bond between two amino acid residues.

Suitable enzyme substrates, antagonists, agonists or inhibitors include glucose and glucose analogues; fatty acids, or elastase, Angiotensin II or metalloproteinase inhibitors. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid.

When the BTM is a peptide, preferred such peptides include Peptide A, Peptide B, Peptide C and Peptide D as defined below, as well as:

somatostatin, octreotide and analogues, peptides which bind to the ST receptor, where ST refers to the heat-stable toxin produced by *E. coli* and other micro-organisms;

bombesin;

vasoactive intestinal peptide;

neurotensin;

laminin fragments e.g. YIGSR (SEQ ID NO: 1), PDSGR (SEQ ID NO: 2),

IKVAV (SEQ ID NO: 3), LRE and KCQAGTFALRGD-PQG (SEQ ID NO: 4),

N-formyl chemotactic peptides for targeting sites of leucocyte accumulation,

Platelet factor 4 (PF4) and fragments thereof, peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);

peptides which are substrates or inhibitors of angiotensin, such as:

angiotensin II Asp-Arg-Val-Tyr-Ile-His-Pro-Phe (SEQ ID NO: 5) (E. C. Jorgensen et al, *J. Med. Chem.*, 1979, Vol 22, 9, 1038-1044)

[Sar, Ile] Angiotensin II: Sar-Arg-Val-Tyr-Ile-His-Pro-Ile (SEQ ID NO: 6) (R. K. Turker et al., *Science*, 1972, 177, 1203).

Angiotensin I: Asp-Arg-Val-Tyr-Ile-His-Pro-Phe-His-Leu (SEQ ID NO: 7).

More preferred BTM peptides are chosen from Peptide A, Peptide B, Peptide C and Peptide D as defined below:

(i) Peptide A=an Arg-Gly-Asp peptide;

(ii) Peptide B=an Arg-Gly-Asp peptide which comprises the fragment

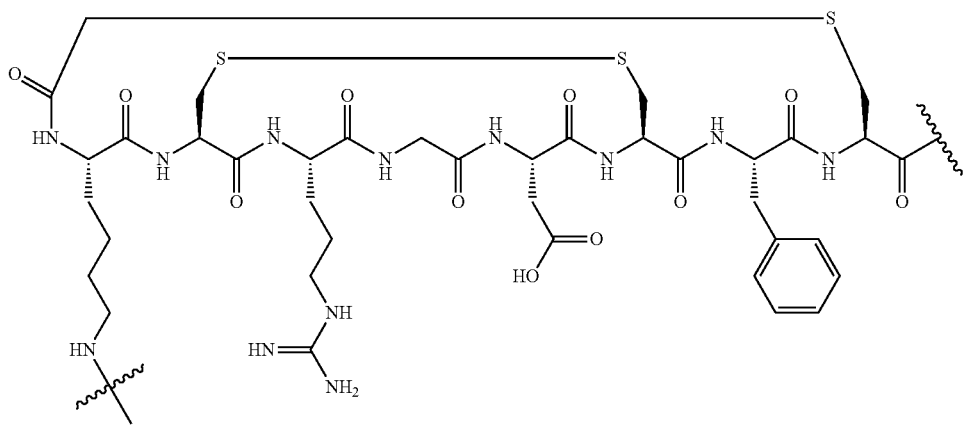 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

(iii) Peptide C=a c-Met binding cyclic peptide which comprises the amino acid sequence:
-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$- (SEQ ID NO: 8)
wherein X$^1$ is Asn, His or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds;

(i) Peptide D=a lantibiotic peptide of formula:
Cys$^a$-Xaa-Gln-Ser$^b$-Cys$^c$-Ser$^d$-Phe-Gly-Pro-Phe-Thr$^c$-Phe-Val-Cys$^b$-(HO-Asp)-Gly-Asn-Thr$^a$-Lys$^d$ (SEQ ID NO: 9)
wherein Xaa is Arg or Lys;
Cys$^a$-Thr$^a$, Ser$^b$-Cys$^b$ and Cys$^c$-Thr$^c$ are covalently linked via thioether bonds;
Ser$^d$-Lys$^d$ are covalently linked via a lysinoalanine bond;
HO-Asp is ß-hydroxyaspartic acid.
Especially preferred BTM peptides are Peptide B, Peptide C and Peptide D.
A most preferred such Peptide B peptide is of formula (A):

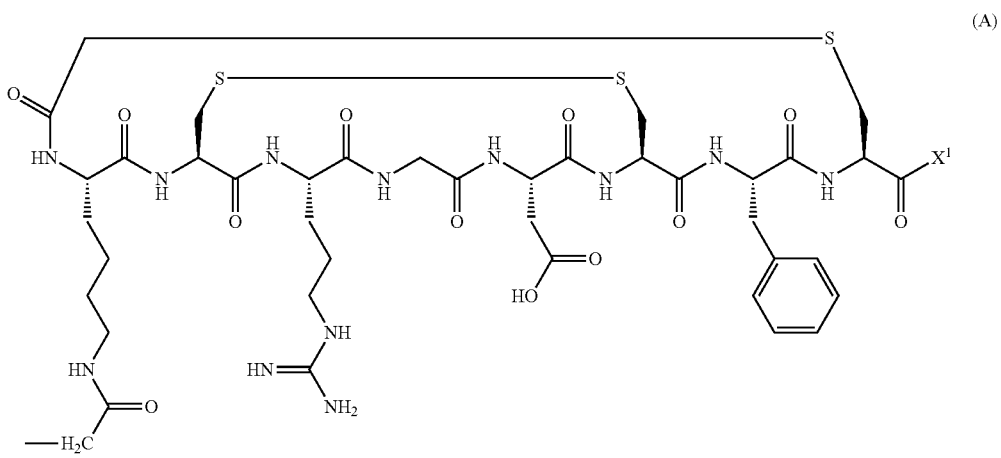

(A)

wherein X$^1$ is either —NH$_2$ or

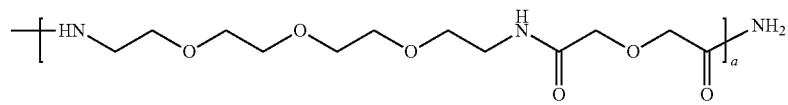

wherein a is an integer of from 1 to 10.
In Formula A, a is preferably 1.

A preferred c-Met binding cyclic peptide has the sequence:

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys (SEQ ID NO: 10).

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)R$^G$ where the acyl group —(C=O)R$^G$ has R$^G$ chosen from: $C_{1-6}$ alkyl, $C_{3-10}$ aryl groups or comprises a polyethyleneglycol (PEG) building block. Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tert-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide In Formula IA, the $X^1$ group is suitably attached to a functional group of the BTM as described below. Thus, N-(1-Ethoxyethylidene)-2-aminooxyacetic acid N-hydroxysuccinimidyl ester (Eei-AOAc-OSu) is commercially available from Iris Biotech GmbH (Waldershofer Str. 49-51, 95615 Marktredwitz, Germany) That Eei-protected aminooxy active ester can be conjugated directly to an amine-containing BTM (e.g. having a Lys residue), to give a protected compound of Formula IA. The aminooxy-functionalised maleimide Mal-AO has been described by Padilla de Jesus et al [U.S. Pat. No. 7,902,332 and Mol. Imaging Biol., 10, 177-181 (2008)]:

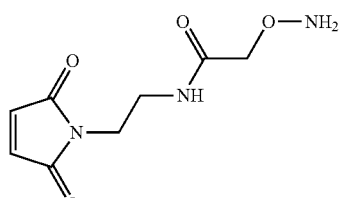

Mal-AO

The bifunctional linker Mal-AO can be used to attach aminooxy functional groups to thiol-containing BTMs, by selective reaction of said thiol with the maleimide function of Mal-AO. Padilla de Jesus (cited above), apply this to the conjugation of a HER2 selective Affibody.

Further routes to Eei-protected peptides are described by Dulery et al [Tetrahedron, 63, 11952-11958 (2007)] and Foillard et al [J. Org. Chem., 73, 983-991 (2008)]. Dulery and Foillard also describe suitable conditions for deprotection of the Eei protecting group.

In a second aspect, the present invention provides a lyophilised composition which comprises the lyophilised aminooxy compound of Formula IIA as defined in step (iii) of the first aspect.

Preferred embodiments of the purified aminooxy compound of Formula IIA in the second aspect are as described in the first aspect (above).

The lyophilised composition of the second aspect excludes aldehydes and ketones.

The lyophilised composition of the second aspect preferably excludes residual TFA, since residual TFA can reduce the stability of some aminooxy compounds of Formula IIA.

The lyophilised composition of the second aspect is important because, for further reaction, in particular for radiolabelling as described in the third aspect, a much more concentrated form is needed. The lyophilised composition can also be obtained sterile—which is important when radiopharmaceutical compositions are to be prepared therefrom. This is described in the third aspect (below). The lyophilised composition can advantageously be used in automated synthesizers and associated cassettes, as described in the fourth, fifth and sixth aspects (below).

The lyophilised composition may optionally contain one or more additional excipients chosen from: a filler to facilitate lyophilisation or a solubiliser.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

By the term "solubiliser" is meant an additive present in the composition which increases the solubility of the agent in the reconstitution solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooloeate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin.

In a third aspect, the present invention provides a method of radiolabelling a biological targeting molecule with $^{18}F$, which comprises:
(a) carrying out the method of the first aspect to give the lyophilised composition of the second aspect;
(b) condensation of said lyophilised composition from step (a) with a carbonyl compound of Formula IIIA in a suitable solvent:

$$Q\text{-[linker]-}(C=O)Y^1 \qquad (IIIA);$$

to give a radiolabelled conjugate of Formula (IVA):

$$[BTM]\text{-}O\text{-}N=(CY^1)\text{-[linker]-}Q \qquad (IVA)$$

where:
Q is a group which comprises the radioisotope $^{18}F$;
[BTM] is the biological targeting molecule as defined in the first aspect;
$Y^1$ is H, $C_{1-6}$ alkyl or $C_{4-10}$ aryl,
[linker] is a linker group.

Preferred embodiments of the aminooxy compound of Formula IIA, BTM, $Y^1$ and [linker] in the third aspect are as described in the first aspect (above). Preferred embodiments of the lyophilised composition in the third aspect are as described in the second aspect (above).

The term "group which comprises a radioisotope" means that either a functional group comprises the radioisotope, or the radioisotope is attached as an additional species. When a functional group comprises the radioisotope, this means that the chemical structure already contains the chemical element in question, and the radioactive isotope of that element present at a level significantly above the natural abundance level of said isotope. Such elevated or enriched levels of isotope are suitably at least 5 times, preferably at least 10 times, most preferably at least 20 times; and ideally either at least 50 times the natural abundance level of the isotope in question, or present at a level where the level of enrichment of the isotope in question is 90 to 100%. Examples of such functional groups include fluoroalkyl groups with elevated levels of $^{18}F$, such that the $^{18}F$ atom is within the chemical structure.

By the term "linker group" is meant a bivalent group of formula $-(A)_m-$ wherein each A is independently $-CR_2-$, $-CR=CR-$, $-C\equiv C-$, $-CR_2CO_2-$, $-CO_2CR_2-$, $-NRCO-$, $-CONR-$, $-NR(C=O)NR-$, $-NR(C=S)NR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, or a $C_{3-12}$ heteroarylene group, wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

and m is an integer of value 1 to 20.

In the third aspect, $Y^{1'}$ is preferably H i.e. the carbonyl compound of Formula IIIA is an aldehyde. A preferred carbonyl compound of Formula IIIA is $^{18}F$-4-fluorobenzaldehyde.

The condensation step (b) of the third aspect is preferably carried out in the presence of aniline or a salt thereof (e g aniline hydrochloride). The use of aniline in oxime ligations has been shown to be effective in increasing the overall reaction rate and to allow such reactions to occur at less acidic pH values [Dirksen, et al., Angew. Chem. Int. Ed. Engl., 45, 7581-7584 (2006)]. After step (b) of the method of the third aspect, the product conjugate of Formula IVA may preferably be separated and/or purified using standard techniques such as chromatography.

The method of preparation of the third aspect is preferably carried out such that the $^{18}F$-labelled biological targeting molecule is obtained as a radiopharmaceutical composition which comprises said $^{18}F$-labelled biological targeting molecule, together with a biocompatible carrier in a form suitable for mammalian administration. $^{18}F$ has the advantage that it is suitable for Positron Emission Tomography (PET) imaging.

By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

The "biocompatible carrier" is a fluid, especially a liquid, in which the radioconjugate can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection, isotonic saline or phosphate buffer.

The radiolabelled conjugate and biocompatible carrier are supplied in a suitable vial or vessel which comprises a sealed container which permits maintenance of sterile integrity and/or radioactive safety, plus optionally an inert headspace gas (e.g. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (e.g. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 50 cm$^3$ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use.

The radiopharmaceutical composition may contain additional optional excipients such as: an antimicrobial preservative, pH-adjusting agent, filler, radioprotectant, solubiliser or osmolality adjusting agent. The terms "filler" and "solubiliser" are as defined in the second aspect (above). By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. By the term "biocompatible cation" ($B^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

In order to obtain radiopharmaceutical compositions, the method of the third aspect may be carried out in various ways:
 a) aseptic manufacture techniques in which the steps are carried out in a clean room environment;
 b) terminal sterilisation, in which steps (i)-(iii) of the first aspect are carried out without using aseptic manufacture, and then sterilised as the last step [e.g. by gamma irradiation, autoclaving dry heat or chemical treatment (e.g. with ethylene oxide)];
 c) kit methodology in which a sterile, non-radioactive kit formulation comprising the lyophilised composition of the second aspect, together with optional excipients is reacted with the radioactive compound of Formula IIIA;
 d) aseptic manufacture techniques in which the steps are carried out using an automated synthesizer apparatus.

Method (d) is preferred. Thus, the method of the third aspect is preferably carried out using an automated synthesizer apparatus. Such automated synthesizers are described in the fourth aspect (below).

The carbonyl compound of Formula IIIA can be obtained as follows. The $^{18}F$-fluorinated aldehyde may be $^{18}F$-fluorobenzaldehyde or p-(di-tert-butyl-$^{18}F$-fluorosilyl)benzaldehyde ($^{18}F$-SiFA-A). $^{18}F$-labelled aliphatic aldehydes of formula $^{18}F(CH_2)_2O[CH_2CH_2O]_qCH_2CHO$, where q is 3, can be obtained by the method of Glaser et al [Bioconj. Chem., 19(4), 951-957 (2008)]. $^{18}F$-fluorobenzaldehyde can be obtained by the method of Glaser et al [J. Lab. Comp. Radiopharm., 52, 327-330 (2009)]. The precursor to $^{18}F$-fluorobenzaldehyde, i.e. $Me_3N^+$—$C_6H_4$—CHO. $CF_3SO_3^-$ can be obtained by the method of Haka et al [J. Lab. Comp. Radiopharm., 27, 823-833 (1989)].

The carbonyl compound of Formula IIIA may optionally be generated in situ by deprotection of a suitable protected derivative. The use of carbonyl protecting groups is described in *Protective Groups in Organic Synthesis, 4th Edition*, Theorodora W. Greene and Peter G. M. Wuts, [Wiley Blackwell, (2006)].

In a fourth aspect, the present invention provides an automated synthesizer apparatus which comprises the lyophilised composition of the second aspect.

Preferred embodiments of the purified aminooxy compound of Formula IIA and lyophilised composition in the fourth aspect are as described in the first and second aspects respectively (above).

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette.

By the term "cassette" is meant a unit piece of apparatus designed such that the whole unit fits removably and interchangeably onto an automated synthesizer apparatus (as defined above), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid phase extraction or SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single use cassette which comprises all the reagents, reaction vessels and apparatus necessary to carry out the preparation of a given batch of radiofluorinated radiopharmaceutical. The cassette means that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In a fifth aspect, the present invention provides the use of an automated synthesizer apparatus to carry out the method of preparation of the first aspect, or the method of radiolabelling of the third aspect.

Preferred embodiments of the purified aminooxy compound of Formula IIA and purification method in the fifth aspect are as described in the first aspect (above). Preferred embodiments of the method of radiolabelling in the fifth aspect are as described in the third aspect (above).

In a sixth aspect, the present invention provides a single-use, disposable cassette suitable for use in the automated synthesizer of the fourth aspect, wherein said cassette comprises the lyophilised composition of the second aspect.

Preferred aspects of the automated synthesizer and cassette in the sixth aspect are as described in the fourth aspect (above). Preferred aspects of the aminooxy compound of Formula IIA in the sixth aspect, are as described in the first aspect. Preferred aspects of the lyophilised composition in the sixth aspect, are as described in the second aspect (above).

The invention is illustrated by the non-limiting Examples detailed below:

Example 1 provides the synthesis of a c-Met targeting peptide of the invention ("Peptide 1").

Example 2 provides the synthesis of an aminooxy-functionalised Peptide 1 ("Compound 2"), wherein the aminooxy functional group is protected with a protecting group (Eei).

Example 3 provides the synthesis of a bifunctional aminooxy maleimide linker (Compound 4).

Example 4 provides the synthesis, purification and lyophilisation of an aminooxy-functionalised Affibody (Compound 6), via reaction of an Affibody with Compound 4.

Example 5 provides the $^{18}F$ labelling of Compound 6, showing that the method of the present invention provides viable radiolabelling precursors.

Example 6 shows that the method of the present invention (Method 2) provides

Compound 2 of improved purity compared to when the previous method (Method 1) was used. Method 2 also provided lyophilised material which was more readily soluble in the solvents for radiolabelling. The impact of the latter was that the purification time for Compound 3 was reduced by 31% (1287 seconds vs 885 seconds using a FastLab™ radiosynthesizer apparatus). The RCP of Compound 3 obtained when precursor prepared by Method 2 was as good as for Method 1, and the non-radioactive peptidic impurities (total peptide content) in Compound 3 were decreased by 26%.

Compounds of the Invention

| Name | Structure |
|---|---|
| Peptide 1 | Disulfide bridges at Cys4-16 and Cys6-14;<br>Ac-Ala-Gly-Ser-Cys-Tyr-Cys-Ser-Gly-Pro-Pro-Arg-Phe-Glu-Cys-Trp-Cys-Tyr-Glu-Thr Glu-Gly-Thr-Gly-Gly-Gly-Lys-NH$_2$ (SEQ ID NO: 11) or<br>Ac-AGSCYCSGPPRFECWCYETEGTGGGK-NH$_2$ (SEQ ID NO: 11) |
| Compound 1 | [Peptide 1]-NH(CO)—(CH$_2$)—O—N=C(CH$_3$)(OCH$_2$CH$_3$) |
| Compound 2 | [Peptide 1]-NH(CO)—(CH$_2$)—O—NH$_2$ |
| Compound 3 | [Peptide 1]-NH—C(O)—CH$_2$—O—N=CH—C$_6$H$_4$—$^{18}F$ (structure shown) |
| Compound 4 | Bifunctional aminooxy maleimide linker (structure shown) |
| Affibody 1 | AEAKYAKEMRNAYWEIALLPNLTNQQKRAFIRKLYDDPSQSSELLSEAKKLND SQAPKVDC (SEQ ID NO: 12) |
| Compound 5 | Affibody 1 conjugated via maleimide-thiol linkage (structure shown) |

-continued

| Name | Structure |
|---|---|
| Compound 6 | H₂N-O-CH₂-C(=O)-NH-CH₂CH₂-N(succinimide)-S-[Affibody 1] |
| Compound 7 | ¹⁸F-C₆H₄-CH=N-O-CH₂-C(=O)-NH-CH₂CH₂-N(succinimide)-S-[Affibody 1] | where:

Compounds 1, 2 and 3 are functionalised at the epsilon amine group of the carboxy terminal Lys of Peptide 1;

Affibody 1 is selective for HER2;

the S atom of Compounds 5, 6 and 7 is from the terminal Cys residue of Affibody 1.

Abbreviations

Conventional single letter or 3-letter amino acid abbreviations are used.

Ac: Acetyl
Acm: Acetamidomethyl
ACN: Acetonitrile
AcOH: Acetic acid.
Boc: tert-Butyloxycarbonyl
tBu: tertiary-butyl
DCM: Dichloromethane
DIPEA: N,N-Diisopropylethyl amine
DMF: Dimethylformamide
DMSO: Dimethylsulfoxide
Eei: ethoxyethylidine;
Eei-AOAc-OSu: N-(1-Ethoxyethylidene)-2-aminooxy-acetic acid N-hydroxysuccinimidyl ester;
Fmoc: 9-Fluorenylmethoxycarbonyl;
HBTU: O-Benzotriazol-1-yl-N,N,N',N'-tetramethyluronium hexafluorophosphate;
HPLC: High performance liquid chromatography;
MW: molecular weight;
NHS: N-hydroxy-succinimide;
NMM: N-Methylmorpholine;
NMP: 1-Methyl-2-pyrrolidinone;
Pbf: 2,2,4,6,7-Pentamethyldihydrobenzofuran-5-sulfonyl;
RP-HPLC: reverse-phase high performance liquid chromatography;
SPE: solid phase extraction;
tBu: tert-butyl;
TFA: Trifluoroacetic acid;
THF: Tetrahydrofuran;
TIS: Triisopropylsilane;
Trt: Trityl.

Example 1: Synthesis of Peptide 1

Step (a): Synthesis of Protected Precursor Linear Peptide. The precursor linear peptide has the structure:
Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Lys-NH$_2$ (SEQ ID NO: 13)

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr($\Psi^{Me,Me}$pro)-Glu(OtBu)-Gly-Thr(tBu)-Gly-Gly-Gly-Lys(Boc)-Polymer (SEQ ID NO: 14) was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide 1 linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min) Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge.

Cys4-16; Ac-Ala-Gly-Ser-Cys-Tyr-Cys(Acm)-Ser-Gly-Pro-Pro-Arg-Phe-Glu-Cys(Acm)-Trp-Cys-Tyr-Glu-Thr-Glu-Gly-Thr-Gly-Gly-Gly-Lys-NH$_2$ (SEQ ID NO: 15).

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 44 min) of the residue afforded 72 mg of pure Peptide 1 monocyclic precursor. The pure product (as a mixture of isomers P1 to P3) was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 5.37 min (P1); 5.61 min (P2); 6.05 min (P3)). Further product characterisation was carried out using electrospray mass spectrometry (MH$_2^{2+}$ calculated: 1463.6, MH$_2^{2+}$ found: 1464.1 (P1); 1464.4 (P2); 1464.3 (P3)).

Step (c): Formation of Second Cys6-14 Disulfide Bridge (Peptide 1).

The monocyclic precursor from step (b) (72 mg) was dissolved in 75% AcOH/water (72 mL) under a blanket of nitrogen. 1 M HCl (7.2 mL) and 0.05 M I$_2$ in AcOH (4.8 mL) were added in that order and the mixture stirred for 45 min 1 M ascorbic acid (1 mL) was added giving a colourless mixture. Most of the solvents were evaporated in vacuo and the residue (18 mL) diluted with water/0.1% TFA (4 mL) and the product purified using preparative HPLC. Purification by preparative HPLC (gradient: 0% B for 10 min, then 20-30% B over 40 min where A=H$_2$O/0.1% TFA and B=ACN/0.1% TFA, flow rate: 10 mL/min, column: Phenomenex Luna 5μ C18 (2) 250×21.20 mm, detection: UV 214 nm, product retention time: 43-53 min) of the residue afforded 52 mg of pure Peptide 1. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 6.54 min) Further product characterisation was carried out using electrospray mass spectrometry (MH$_2^{2+}$ calculated: 1391.5, MH$_2^{2+}$ found: 1392.5).

Example 2: Synthesis, Purification and Lyophilisation of Compound 2

Peptide 1 (0.797 g) and Eei-AOAc-OSu (IRIS Biotech; 127 mg) were dissolved in DMF (12 mL). DIPEA (100 μL) was added and the reaction mixture shaken for 26 min. A second aliquot of DIPEA (80 μL) was added and the reaction mixture shaken for 2 hr. The reaction mixture was then diluted with 10% ACN/water/0.1% ammonium acetate (40 mL), and the product purified by preparative HPLC using A=0.1% TFA/water and B=ACN with gradient elution of 20-40% B over 40 min. The fractions containing pure products (these are a mixture of Compound 1 and Compound 2) were pooled in a flask and the flask flushed with argon. The solution was stirred overnight to afford complete removal of Eei protection groups. The deprotected product was lyophilised affording 550 mg (69% yield) of Compound 2.

The pure product was analysed by analytical LC-MS (gradient: 10-40% B over 5 min where A=H$_2$O/0.1% TFA and B=ACN TFA, flow rate: 0.6 mL/min, column: Phenomenex Luna 3μ C18 (2) 20×2 mm, detection: UV 214 nm, product retention time: 3.00 min), MH$_2^{2+}$ calculated: 1428.1, MH$_2^{2+}$ found: 1427.9).

Example 3: Synthesis of Bifunctional Linker (Compound 4)

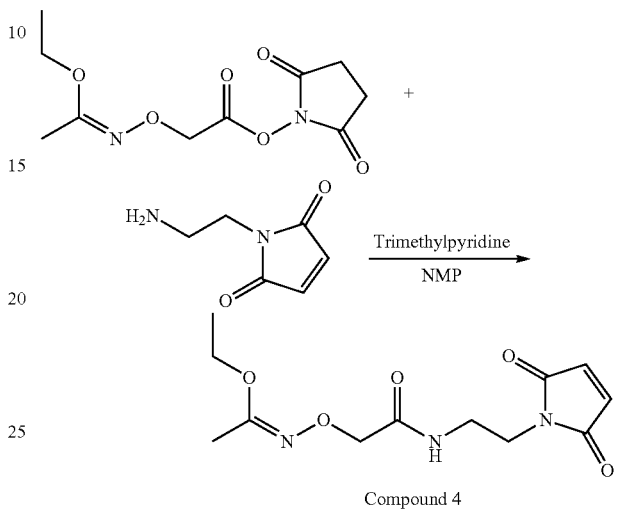

Compound 4

N-(2-aminoethyl)maleimide TFA-salt (Sigma-Aldrich; 151 mg.) and Eei-AOAc-OSu (IRIS Biotech; 77 mg) were stirred in NMP (2 mL) at ambient temperature. Trimethylpyridine (80 μL) was added, and the reaction mixture stirred at ambient temperature for 70 min. The reaction was quenched by dilution with 0.1% acetic acid (7 mL). The product was purified by preparative HPLC as follows:

| | |
|---|---|
| Detection | UV at 214 nm and 254 nm |
| Column type and size | Luna C-18 (2), 5 μm, 100 Å, 20 × 250 mm from Phenomenex |
| Eluent A | 0.1% v/v acetic acid in water, 1 mL/L |
| Eluent B | Acetonitrile (Lichrosolv) |
| Gradient | 15-30% B during 40 min. |
| Flow rate | 10 ml/min during gradient elution |

The purified Compound 4 was freeze-dried. Yield 43 mg (75%), purity: >97% by area.

The pure product was analysed by analytical LC-MS (gradient: 10-40% B over 5 min where A=H$_2$O/0.1% TFA and B=ACN/0.1% TFA, flow rate: 0.6 mL/min, column: Phenomenex Luna 3μ C18 (2) 20×2 mm, detection: UV 214 nm, product retention time: 1.93 min), MH$^+$ calculated: 284.1, MH$^+$ found: 284.1).

Example 4: Synthesis, Purification and Lyophilisation of Compound 6

Step (a): Synthesis of Compound 5.

Affibody 1 (Affibody AB; 1.00 g) and Compound 4 (81 mg) were dissolved in 30% aqueous acetonitrile. Ammonium acetate was added to adjust the pH to 6. The mixture was then stirred at ambient temperature for 34 min, by which time the reaction was complete (monitoring by LC-MS).

Step (b): Purification of Compound 5.

The reaction mixture from step (a) was diluted with water (20 mL). The diluted mixture was purified by preparative HPLC as follows:

| Parameter | Conditions |
|---|---|
| Detection | UV at 214 nm and 254 nm |
| Column | Luna C-18 (2), μm, 100 Å, 50 × 250 mm Axia packed from Phenomenex |
| Eluent A | 0.1% (volume) TFA in water, 1 ml/l |
| Eluent B | Acetonitrile (Lichrosolv) |
| Equilibration | 15-20 min at 50 ml/min (not a part of the gradient method) |
| Gradient | 15-35% B during 50 min, 35-95% B during 2 min and 95% B (isocratic wash during 8-15 min) |
| Flow rate | 50 ml/min during gradient elution |

Compound 5 was eluted by applying the desired gradient and showed a retention time of ca. 35 minutes.

Step (c): Deprotection of Compound 5 to give Compound 6.

The purified fractions (ca. 0.5 L) from step (b) were combined. These are a mixture of Compound 5 and Compound 6. TFA (5 mL) was added, and the reaction mixture stirred at ambient temperature under argon, monitoring by HPLC. The deprotection was complete within 105 minutes.

Step (d): Lyophilisation of Purified Compound 6.

The deprotected Compound 6 solution from step (c) was then frozen whilst flushing the flask with a gentle stream of argon. The frozen Compound 6 solution was then freeze-dried. Yield: 1.01 g (98%), purity: 89 area % HPLC.

The pure product was analysed by analytical HPLC (gradient: 10-40% B over 5 min where A=$H_2O$/0.1% TFA and B=ACN/0.1% TFA, flow rate: 0.6 mL/min, column: Phenomenex Luna 3μ C18 (2) 20×2 mm, detection: UV 214 nm, product retention time: 3.13 min) and by MS ($MH_8^{8+}$ calculated: 906.2, $MH_8^{8+}$ found: 906.3).

Example 5: Radiosynthesis of Compound 7

Step (a): Synthesis of [$^{18}$F]-fluorobenzaldehyde ($^{18}$F-FBA).

[$^{18}$F]-fluoride was produced using a GEMS PETtrace cyclotron with a silver target via the [$^{18}$O](p,n) [$^{18}$F]nuclear reaction. Total target volumes of 1.5-3.5 mL were used. The radiofluoride was trapped on a Waters QMA cartridge (pre-conditioned with carbonate), and the fluoride is eluted with a solution of Kryptofix$_{2.2.2}$ (4 mg, 10.7 μM) and potassium carbonate (0.56 mg, 4.1 μM) in water (80 μL) and acetonitrile (320 μL). Nitrogen was used to drive the solution off the QMA cartridge to the reaction vessel. The [$^{18}$F]-fluoride was dried for 9 minutes at 120° C. under a steady stream of nitrogen and vacuum. Trimethylammonium benzaldehyde triflate, [Haka et al, J. Lab. Comp. Radiopharm., 27, 823-833 (1989)] (3.3 mg, 10.5 μM), in DMSO (1.1 mL) was added to the dried [$^{18}$F]-fluoride, and the mixture heated at 105° C. for 7 minutes to produce 4-[$^{18}$F]-fluorobenzaldehyde.

Step (b): Conjugation of $^{18}$F-FBA to Compound 6.

Lyophilised Compound 6 from Example 4(d) was radio-labelled with $^{18}$F using $^{18}$F-FBA from Step (a) and a FastLab™ radiosynthesizer apparatus (GE Healthcare Ltd), giving Compound 7 in a yield of 25% and RCP of 95%.

Example 6: Synthesis, Lyophilisation and Radiofluorination of Compound 2 to Give Compound 3—Comparison of Current Method with Previous Methods A lyophilised composition of Compound 2 as a Final Intermediate ("FI") ready for radiofluorination was prepared according to a prior process (Scheme 1), and the method of the present invention (Scheme 2), and the results compared. The two methods are summarised in Schemes 1 and 2:

Scheme 1: Flow chart previous process method (Method 1).

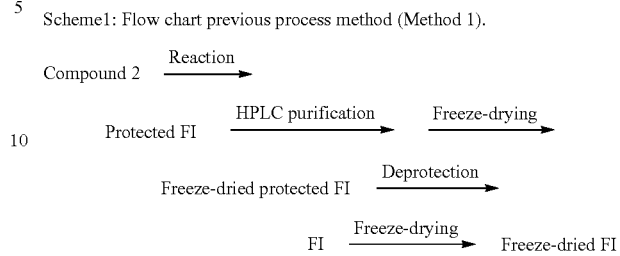

Scheme 2: Flow chart previous invention method (Method 2).

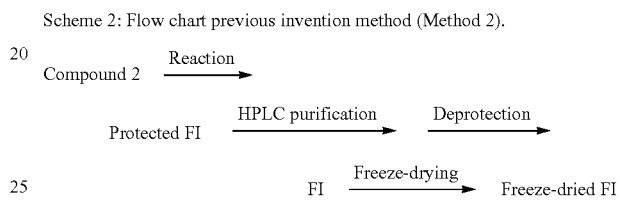

In Schemes 1 and 2, the 'protected FI' corresponds to Compound 1, and 'FI' corresponds to Compound 2.

The purity and the water and TFA content of the freeze-dried products of Methods 1 and 2 were measured. The Method 1 and Method 2 lyophilised materials were then used for radiofluorination with $^{18}$F-FBA according to the method of Example 5, and the radiochemical purity of the Compound 3 determined. The radioactive peptide content of the Compound 3 product was also determined by analytical HPLC.

The data generated are summarised in Table 1:

TABLE 1

Method 1 and Method 2 Data.

| | Compound 2 | | | Compound 3 | |
|---|---|---|---|---|---|
| | TFA content | Water content | Purity (by HPLC) | RCP | Peptide Impurity Content* |
| Method 1 | 12.7% m/m | 4.7% m/m | 91.9% | >90% | 18.2 μg (average of 20 experiments) |
| Method 2 (present invention). | 7.6% m/m | 4.6% m/m | 94.3% | >90% | 13.4 μg (average of 10 experiments) |

*this is for the product eluting from the FASTlab where: m/m means mass/mass.

The invention claimed is:

1. A method of preparing an aminoxy-functionalized biological targeting molecule (BTM) lyophilized composition, which comprises:

(i) purifying with reverse phase chromatography Compound IA:

[BTM]-$X^1$ (IA), wherein [BTM] is a biological targeting molecule; $X_1$ is a protected aminooxy group of formula:

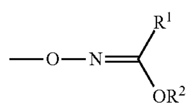

wherein $R^1$ and $R^2$ are independently chosen from $C_{1-3}$ alkyl, $C_{1-3}$ fluoroaryl, or $C_{4-6}$ aryl, the reverse phrase chromatography using an acidic mobile phase that comprises aqueous trifluoroacetic acid, resulting in a purified mixture comprising greater than 10% Compound IA and an amount of Compound IIA:

[BTM]-O—$NH_2$ (IIA)

(ii) further reacting the purified mixture after step (i) with the acidic mobile phase until at least 90% of the purified Compound IA is converted to Compound IIA, resulting in a Compound IIA solution; and (iii) lyophilizing the Compound IIA solution from step (ii), to give the lyophilized aminooxy-functionalized biological targeting molecule composition.

2. The method of claim 1, where $R^1$ and $R^2$ are independently $C_{1-2}$ alkyl.

3. The method of claim 1, where the BTM comprises a single amino acid, a 3-100 mer peptide, an enzyme substrate, an enzyme antagonist, an enzyme agonist, an enzyme inhibitor, or a receptor-binding compound.

4. The method of claim 1, where the BTM comprises a 3-100 mer peptide which is chosen from Peptide A, Peptide B, Peptide C, or Peptide D as defined below:

(i) Peptide A=an Arg-Gly-Asp peptide;

(ii) Peptide B=an Arg-Gly-Asp peptide which comprises the fragment (iii) Peptide C=a c-Met binding cyclic peptide which comprises the amino acid sequence:

-$Cys^a$-$X^1$-$Cys^c$-$X^2$-Gly-Pro-Pro-$X^3$-Phe-Glu-$Cys^d$-Trp-$Cys^b$-Tyr-$X^4$-$X^5$-$X^6$-(SEQ ID NO: 8)

wherein $X^1$ is Asn, His or Tyr;

$X^2$ is Gly, Ser, Thr or Asn;

$X^3$ is Thr or Arg;

$X^4$ is Ala, Asp, Glu, Gly or Ser;

$X^5$ is Ser or Thr;

$X^6$ is Asp or Glu;

and $Cys^{a-d}$ are each cysteine residues such that residues a and b as well as c and d are cyclised to form two separate disulfide bonds;

(iv) Peptide D=a lantibiotic peptide of formula:
$Cys^a$-Xaa-Gln-$Ser^b$-$Cys^c$-$Ser^d$-Phe-Gly-Pro-Phe-$Thr^c$-Phe-Val-$Cys^b$-(HO-Asp)-Gly-Asn-$Thr^a$-$Lys^d$ (SEQ ID NO: 9)

wherein Xaa is Arg or Lys;

$Cys^a$-$Thr^a$, $Ser^b$-$Cys^b$ and $Cys^c$-$Thr^c$ are covalently linked via thioether bonds;

$Ser^d$-$Lys^d$ are covalently linked via a lysinoalanine bond;

HO-Asp is ß-hydroxyaspartic acid.

5. The method of claim 1, where the reverse phase chromatographic purification of step (i) comprises HPLC.

6. The method of claim 1, further comprising adding additional trifluoroacetic acid into the mobile phase in step (ii).

7. The method of claim 1, further comprising adding additional trifluoroacetic acid into the mobile phase in step (ii).

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Unknown
<220> FEATURE:
<223> OTHER INFORMATION: Description of Unknown:
      Laminin fragment sequence

<400> SEQUENCE: 1

Tyr Ile Gly Ser Arg
1               5

<210> SEQ ID NO 2
<211> LENGTH: 5
<212> TYPE: PRT
<213> ORGANISM: Unknown
<220> FEATURE:
<223> OTHER INFORMATION: Description of Unknown:
      Laminin fragment sequence

<400> SEQUENCE: 2

Pro Asp Ser Gly Arg
1               5

<210> SEQ ID NO 3
<211> LENGTH: 5
<212> TYPE: PRT
<213> ORGANISM: Unknown
<220> FEATURE:
<223> OTHER INFORMATION: Description of Unknown:
      Laminin fragment sequence

<400> SEQUENCE: 3

Ile Lys Val Ala Val
1               5

<210> SEQ ID NO 4
<211> LENGTH: 15
<212> TYPE: PRT
<213> ORGANISM: Unknown
<220> FEATURE:
<223> OTHER INFORMATION: Description of Unknown:
      Laminin fragment sequence

<400> SEQUENCE: 4

Lys Cys Gln Ala Gly Thr Phe Ala Leu Arg Gly Asp Pro Gln Gly
1               5                   10                  15

<210> SEQ ID NO 5
<211> LENGTH: 8
<212> TYPE: PRT
<213> ORGANISM: Unknown
<220> FEATURE:
<223> OTHER INFORMATION: Description of Unknown:
      Angiotensin II sequence

<400> SEQUENCE: 5

Asp Arg Val Tyr Ile His Pro Phe
1               5

<210> SEQ ID NO 6
<211> LENGTH: 8
<212> TYPE: PRT
<213> ORGANISM: Unknown
<220> FEATURE:
<223> OTHER INFORMATION: Description of Unknown:

```
      Angiotensin II sequence
<220> FEATURE:
<221> NAME/KEY: MOD_RES
<222> LOCATION: (1)..(1)
<223> OTHER INFORMATION: Sarcosine

<400> SEQUENCE: 6

Xaa Arg Val Tyr Ile His Pro Ile
1               5

<210> SEQ ID NO 7
<211> LENGTH: 10
<212> TYPE: PRT
<213> ORGANISM: Unknown
<220> FEATURE:
<223> OTHER INFORMATION: Description of Unknown:
      Angiotensin I sequence

<400> SEQUENCE: 7

Asp Arg Val Tyr Ile His Pro Phe His Leu
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(13)
<223> OTHER INFORMATION: Disulfide bond between residues
<220> FEATURE:
<221> NAME/KEY: MOD_RES
<222> LOCATION: (2)..(2)
<223> OTHER INFORMATION: Asn, His or Tyr
<220> FEATURE:
<221> NAME/KEY: MISC_FEATURE
<222> LOCATION: (3)..(11)
<223> OTHER INFORMATION: Disulfide bond between residues
<220> FEATURE:
<221> NAME/KEY: MOD_RES
<222> LOCATION: (4)..(4)
<223> OTHER INFORMATION: Gly, Ser, Thr or Asn
<220> FEATURE:
<221> NAME/KEY: MOD_RES
<222> LOCATION: (8)..(8)
<223> OTHER INFORMATION: Thr or Arg
<220> FEATURE:
<221> NAME/KEY: MOD_RES
<222> LOCATION: (15)..(15)
<223> OTHER INFORMATION: Ala, Asp, Glu, Gly or Ser
<220> FEATURE:
<221> NAME/KEY: MOD_RES
<222> LOCATION: (16)..(16)
<223> OTHER INFORMATION: Ser or Thr
<220> FEATURE:
<221> NAME/KEY: MOD_RES
<222> LOCATION: (17)..(17)
<223> OTHER INFORMATION: Asp or Glu

<400> SEQUENCE: 8

Cys Xaa Cys Xaa Gly Pro Pro Xaa Phe Glu Cys Trp Cys Tyr Xaa Xaa
1               5                   10                  15

Xaa

<210> SEQ ID NO 9
<211> LENGTH: 19
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MISC_FEATURE
<222> LOCATION: (1)..(18)
<223> OTHER INFORMATION: Thioether bond between residues
<220> FEATURE:
<221> NAME/KEY: MOD_RES
<222> LOCATION: (2)..(2)
<223> OTHER INFORMATION: Arg or Lys
<220> FEATURE:
<221> NAME/KEY: MISC_FEATURE
<222> LOCATION: (4)..(14)
<223> OTHER INFORMATION: Thioether bond between residues
<220> FEATURE:
<221> NAME/KEY: MISC_FEATURE
<222> LOCATION: (5)..(11)
<223> OTHER INFORMATION: Thioether bond between residues
<220> FEATURE:
<221> NAME/KEY: MISC_FEATURE
<222> LOCATION: (6)..(19)
<223> OTHER INFORMATION: Lysinoalanine bond between residues
<220> FEATURE:
<221> NAME/KEY: MOD_RES
<222> LOCATION: (15)..(15)
<223> OTHER INFORMATION: Beta-hydroxyaspartic acid

<400> SEQUENCE: 9

Cys Xaa Gln Ser Cys Ser Phe Gly Pro Phe Thr Phe Val Cys Asp Gly
1               5                   10                  15

Asn Thr Lys

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(16)
<223> OTHER INFORMATION: Disulfide bond between residues
<220> FEATURE:
<221> NAME/KEY: MISC_FEATURE
<222> LOCATION: (6)..(14)
<223> OTHER INFORMATION: Disulfide bond between residues

<400> SEQUENCE: 10

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
            20                  25

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(16)
<223> OTHER INFORMATION: Disulfide bond between residues
<220> FEATURE:
<221> NAME/KEY: MISC_FEATURE
<222> LOCATION: (6)..(14)
<223> OTHER INFORMATION: Disulfide bond between residues

<400> SEQUENCE: 11

Ala Gly Ser Cys Tyr Cys Ser Gly Pro Pro Arg Phe Glu Cys Trp Cys

```
                1               5                   10                  15
Tyr Glu Thr Glu Gly Thr Gly Gly Gly Lys
                    20                  25

<210> SEQ ID NO 12
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
                    20                  25                  30

Lys Leu Tyr Asp Asp Pro Ser Gln Ser Ser Glu Leu Leu Ser Glu Ala
                35                  40                  45

Lys Lys Leu Asn Asp Ser Gln Ala Pro Lys Val Asp Cys
            50                  55                  60

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (14)..(14)
<223> OTHER INFORMATION: Cys(Acm)

<400> SEQUENCE: 13

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
                    20                  25

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(tBu)
<220> FEATURE:
<221> NAME/KEY: MOD_RES
<222> LOCATION: (4)..(4)
<223> OTHER INFORMATION: Cys(Trt)
<220> FEATURE:
<221> NAME/KEY: MOD_RES
<222> LOCATION: (5)..(5)
<223> OTHER INFORMATION: Tyr(tBu)
<220> FEATURE:
<221> NAME/KEY: MOD_RES
<222> LOCATION: (6)..(6)
<223> OTHER INFORMATION: Cys(Acm)
<220> FEATURE:
<221> NAME/KEY: MOD_RES
```

```
<222> LOCATION: (7)..(7)
<223> OTHER INFORMATION: Ser(tBu)
<220> FEATURE:
<221> NAME/KEY: MOD_RES
<222> LOCATION: (11)..(11)
<223> OTHER INFORMATION: Arg(Pbf)
<220> FEATURE:
<221> NAME/KEY: MOD_RES
<222> LOCATION: (13)..(13)
<223> OTHER INFORMATION: Glu(OtBu)
<220> FEATURE:
<221> NAME/KEY: MOD_RES
<222> LOCATION: (14)..(14)
<223> OTHER INFORMATION: Cys(Acm)
<220> FEATURE:
<221> NAME/KEY: MOD_RES
<222> LOCATION: (15)..(15)
<223> OTHER INFORMATION: Trp(Boc)
<220> FEATURE:
<221> NAME/KEY: MOD_RES
<222> LOCATION: (16)..(16)
<223> OTHER INFORMATION: Cys(Trt)
<220> FEATURE:
<221> NAME/KEY: MOD_RES
<222> LOCATION: (17)..(17)
<223> OTHER INFORMATION: Tyr(tBu)
<220> FEATURE:
<221> NAME/KEY: MOD_RES
<222> LOCATION: (18)..(18)
<223> OTHER INFORMATION: Glu(OtBu)
<220> FEATURE:
<221> NAME/KEY: MOD_RES
<222> LOCATION: (19)..(19)
<223> OTHER INFORMATION: Pseudoproline threonine
<220> FEATURE:
<221> NAME/KEY: MOD_RES
<222> LOCATION: (20)..(20)
<223> OTHER INFORMATION: Glu(OtBu)
<220> FEATURE:
<221> NAME/KEY: MOD_RES
<222> LOCATION: (22)..(22)
<223> OTHER INFORMATION: Thr(tBu)
<220> FEATURE:
<221> NAME/KEY: MOD_RES
<222> LOCATION: (26)..(26)
<223> OTHER INFORMATION: Lys(Boc)

<400> SEQUENCE: 14

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
                20                  25

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(16)
<223> OTHER INFORMATION: Disulfide bond between residues
<220> FEATURE:
```

-continued

```
<221> NAME/KEY: MOD_RES
<222> LOCATION: (6)..(6)
<223> OTHER INFORMATION: Cys(Acm)
<220> FEATURE:
<221> NAME/KEY: MOD_RES
<222> LOCATION: (14)..(14)
<223> OTHER INFORMATION: Cys(Acm)

<400> SEQUENCE: 15

Ala Gly Ser Cys Tyr Cys Ser Gly Pro Pro Arg Phe Glu Cys Trp Cys
1               5                   10                  15

Tyr Glu Thr Glu Gly Thr Gly Gly Gly Lys
            20                  25
```